(12) United States Patent
Segawa

(10) Patent No.: US 10,517,468 B2
(45) Date of Patent: Dec. 31, 2019

(54) CAPSULE MEDICAL DEVICE HAVING POSITIONING MEMBER WITH ABUTMENT SURFACES

(71) Applicant: OLYMPUS CORPORATION, Tokyo (JP)

(72) Inventor: Hidetake Segawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 383 days.

(21) Appl. No.: 15/443,201

(22) Filed: Feb. 27, 2017

(65) Prior Publication Data

US 2017/0164820 A1  Jun. 15, 2017

Related U.S. Application Data

(63) Continuation of application No. PCT/JP2016/059718, filed on Mar. 25, 2016.

(30) Foreign Application Priority Data

Apr. 15, 2015 (JP) .................. 2015-083353

(51) Int. Cl.
*A61B 1/04* (2006.01)
*A61B 1/00* (2006.01)
*A61B 5/00* (2006.01)

(52) U.S. Cl.
CPC .......... *A61B 1/041* (2013.01); *A61B 1/00112* (2013.01); *A61B 5/6861* (2013.01); *A61B 2562/162* (2013.01)

(58) Field of Classification Search
CPC ... A61B 1/041; A61B 1/00112; A61B 5/6861; A61B 2562/162
See application file for complete search history.

(56) References Cited

U.S. PATENT DOCUMENTS 8,353,821 B2   1/2013 Segawa
2003/0171653 A1*  9/2003 Yokoi .................... A61B 1/041
                                                        600/160

(Continued)

FOREIGN PATENT DOCUMENTS

CN     101340841 A    1/2009
EP     2 143 367 A1   1/2010

(Continued)

OTHER PUBLICATIONS

Chinese Office Action dated Nov. 1, 2017 in Chinese Patent Application No. 201680002599.X.

(Continued)

*Primary Examiner* — John P Leubecker
(74) *Attorney, Agent, or Firm* — Scully, Scott, Murphy & Presser, P.C.

(57) ABSTRACT

A capsule medical device configured to be introduced into a subject to acquire information about the subject is provided. The capsule medical device includes: a capsule-shaped casing including: a first casing including a hemispherical portion and a cylindrical portion; and a second casing that is a cylindrical casing where an opening edge portion having an opening is positioned at one end, the cylindrical portion of the first casing being fitted on an outer peripheral surface of the second casing on a side of the opening to incorporate an information acquisition member for acquiring information about the subject; and a positioning member including: a first abutment surface configured to abut on an end surface of the second casing on the side of the opening; and a second abutment surface configured to abut on the information acquisition member.

7 Claims, 8 Drawing Sheets

(56) References Cited

U.S. PATENT DOCUMENTS

| | | | |
|---|---|---|---|
| 2004/0176685 A1* | 9/2004 | Takizawa | A61B 1/00036 600/424 |
| 2005/0049462 A1* | 3/2005 | Kanazawa | A61B 1/00096 600/170 |
| 2006/0167339 A1* | 7/2006 | Gilad | A61B 1/00087 600/101 |
| 2006/0252986 A1* | 11/2006 | Akagi | A61B 1/00016 600/101 |
| 2008/0045798 A1 | 2/2008 | Fukuhori | |
| 2008/0255410 A1 | 10/2008 | Okuzumi et al. | |
| 2008/0294143 A1* | 11/2008 | Tanaka | A61B 1/041 604/506 |
| 2010/0016672 A1* | 1/2010 | Segawa | A61B 1/0011 600/173 |
| 2012/0296165 A1 | 11/2012 | Segawa | |
| 2013/0102844 A1* | 4/2013 | Okabe | A61B 1/041 600/109 |
| 2013/0345504 A1 | 12/2013 | Shamir et al. | |
| 2014/0142380 A1* | 5/2014 | Takahashi | A61B 1/0011 600/109 |

FOREIGN PATENT DOCUMENTS

| | | |
|---|---|---|
| EP | 2 356 932 A1 | 8/2011 |
| JP | 2004-065772 A | 3/2004 |
| JP | 2008-043626 A | 2/2008 |
| JP | 2008-272439 A | 11/2008 |
| JP | 4790765 B2 | 10/2011 |
| JP | 5160698 B2 | 3/2013 |
| JP | 5340557 B2 | 11/2013 |

OTHER PUBLICATIONS

Extended Supplementary European Search Report dated Jan. 18, 2018 in European Patent Application No. 16 77 9893.3.
International Search Report dated Jun. 14, 2016 issued in PCT/JP2016/059718.
English Abstract of JP 2008-278962 A, dated Nov. 20, 2008.
English Abstract of WO 2012/073634 Al, dated Jun. 7, 2012.
English Abstract of JP 2008-289900 A, dated Dec. 4, 2008.

* cited by examiner

CAPSULE MEDICAL DEVICE HAVING POSITIONING MEMBER WITH ABUTMENT SURFACES

CROSS-REFERENCE TO RELATED APPLICATIONS

This application is a continuation of PCT international application Ser. No. PCT/JP2016/059718 filed on Mar. 25, 2016 which designates the United States, incorporated herein by reference, and which claims the benefit of priority from Japanese Patent Application No. 2015-083353 filed on Apr. 15, 2015, incorporated herein by reference.

BACKGROUND

1. Technical Field

The disclosure relates to a capsule medical device introduced into an organ of a subject, such as a patient, to obtain information about the subject.

2. Related Art

In endoscopes, a capsule endoscope is known which has an imaging function, a wireless communication function, and the like in a capsule-shaped casing formed in a sufficient size to be introduced into a digestive tract of a subject, such as a patient. This capsule endoscope is swallowed from a mouth of the subject, successively imaging inside the subject to generate image signals while moving in the digestive tract or the like by peristalsis or the like, and wirelessly transmits the image signals to a receiving device outside the subject. The receiving device is carried by the subject, receives in-vivo images wirelessly transmitted by the capsule endoscope introduced into an internal organ of the subject, and stores the received in-vivo images in a recording medium. The in-vivo images stored in the recording medium of the receiving device are captured into an image display device of a workstation or the like. The image display device displays an in-vivo image group of the subject obtained through the recording medium. A doctor, a nurse, or the like observes the in-vivo images displayed on the image display device to diagnose the subject.

The capsule endoscope has a configuration in which a capsule-shaped casing includes a transparent optical dome (transparent casing) and a cylindrical body portion (cylindrical casing) where the transparent optical dome is mounted to an end portion of the cylindrical body portion on a side of an opening of the cylindrical body portion, and the capsule-shaped casing incorporates an illumination unit such as LEDs illuminating inside an organ through the optical dome, an optical unit such as a lens focusing light reflected from inside an organ illuminated by the illumination unit, and an information acquisition member for acquiring information about the subject from an image sensor such as a CCD capturing an image inside an organ (i.e., in-vivo image) formed by the optical unit (e.g., see JP 5340557 B2, JP 5160698 B2, and JP 4790765 B2). Such a capsule endoscope is required to have a structure for positioning an optical pupil center of the optical unit and a spherical center of a dome portion (hemispherical portion), in order to prevent flare. Furthermore, it is necessary to reduce a wall thickness of the casing as an exterior to increase an inner space, for reduction in size and high functionality of the capsule endoscope. Still furthermore, it is desired to reduce the weight of the casing so that the capsule endoscope has a density closer to a density of a liquid inside the digestive tract, for smooth movement of the capsule endoscope in the subject. In addition, it is desired that the capsule endoscope has an outer surface of a smooth shape to facilitate swallowing by the subject.

FIG. 6 is a cross-sectional view illustrating a configuration of a main portion of a capsule endoscope disclosed in JP 5340557 B2. In a capsule endoscope 301 illustrated in FIG. 6, a positioning member 307 is provided to position an optical pupil center of an optical unit 304 and a spherical center of an optical dome portion 321, achieving reduction in wall thickness of the optical dome portion 321 and a cylindrical body portion 322 (e.g., wall thickness $D_3$) to reduce the weight of a casing 302.

FIG. 7 is a cross-sectional view illustrating a configuration of a main portion of a capsule endoscope disclosed in JP 5160698 B2. A capsule endoscope 401 illustrated in FIG. 7 adopts a configuration in which an optical dome portion 421 of a casing 402 has a large thickness to provide abutment surfaces 421a and 421b for abutment of an end surface 422a of a cylindrical body portion 422 on the abutment surface 421a, and for abutment of an end surface 430a of a spacer 430 on the abutment surface 421b, and each member is positioned.

FIG. 8 is a cross-sectional view illustrating a configuration of a main portion of a capsule endoscope disclosed in JP 4790765 B2. A capsule endoscope 501 illustrated in FIG. 8 adopts a bonding method capable of ensuring water-tightness in a short time, in which an inner peripheral surface 521a of an optical dome portion 521 is fitted on an outer peripheral surface 522a of a cylindrical body portion 522 to be subjected to not conventional thermal bonding using a thermosetting adhesive, but UV bonding or laser welding through the optical dome portion 521 on the outside.

SUMMARY

In some embodiments, a capsule medical device includes: a capsule-shaped casing including: a first casing including: a hemispherical portion formed of a transparent member; and a cylindrical portion including an end portion connected to the hemispherical portion and having a diameter the same as that of the hemispherical portion; and a second casing that is a cylindrical casing where an opening edge portion having an opening is positioned at one end, the cylindrical portion being fitted on an outer peripheral surface of the opening edge portion to incorporate an information acquisition member for acquiring information about the subject; and a positioning member including: a first abutment surface configured to abut on an end surface of the opening edge portion; and a second abutment surface configured to abut on the information acquisition member.

The above and other features, advantages and technical and industrial significance of this disclosure will be better understood by reading the following detailed description of presently preferred embodiments of the disclosure, when considered in connection with the accompanying drawings.

DETAILED DESCRIPTION

Description of Embodiments

A preferred embodiment of a capsule medical device according to the disclosure will be described below in detail with reference to the drawings. Note that, in the following, a capsule endoscope configured to be inserted into a subject, and having an imaging function for capturing an in-vivo image as an example of in-vivo information about a subject, and a wireless communication function for wirelessly transmitting the captured in-vivo image is described as an example of the capsule medical device according to the disclosure, but the disclosure is not limited to this embodiment.

Embodiment

Figure 1:
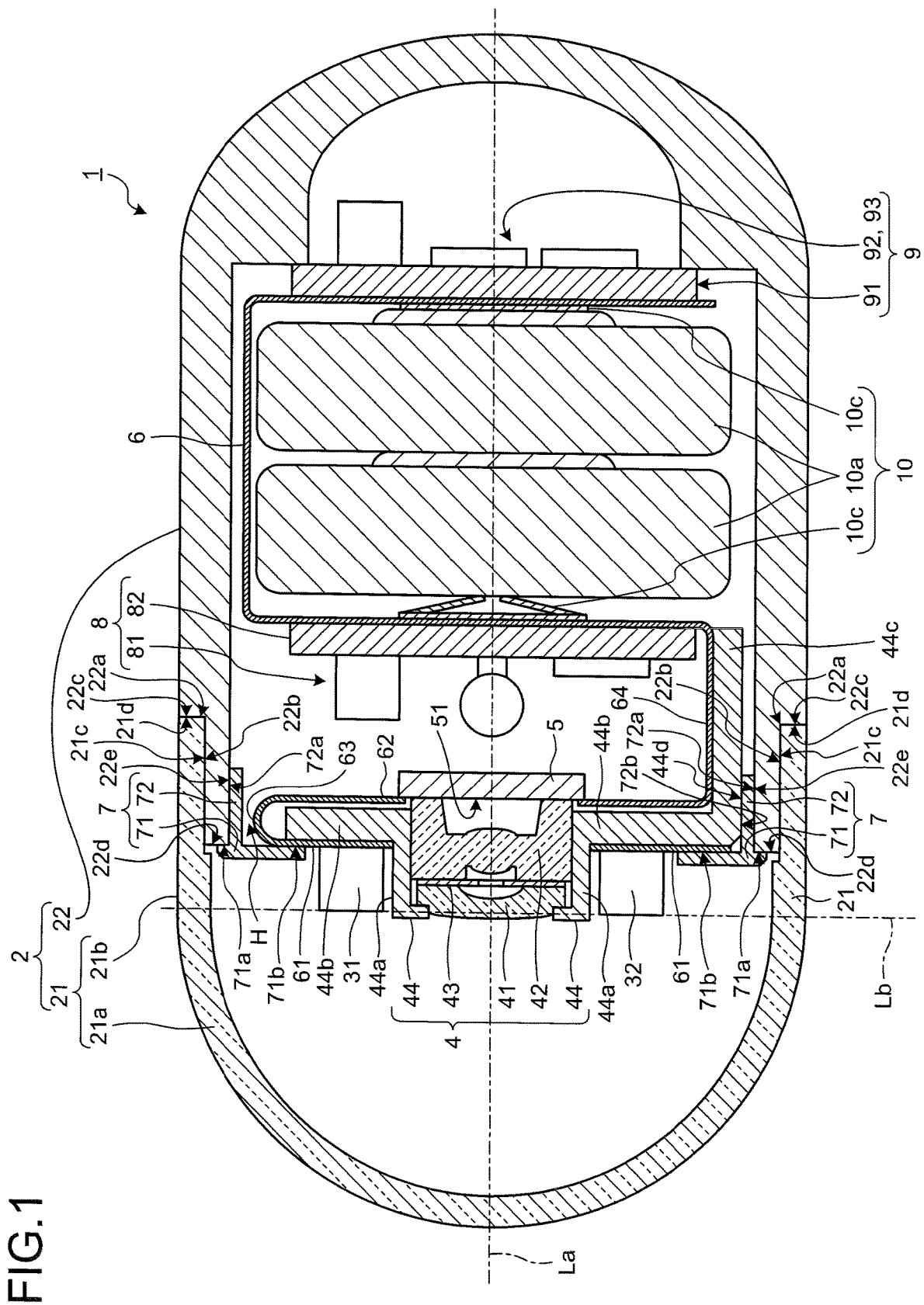
FIG. 1 is a vertical cross-sectional schematic view illustrating an exemplary configuration of a capsule endoscope according to an embodiment of the disclosure.
Figure 2:
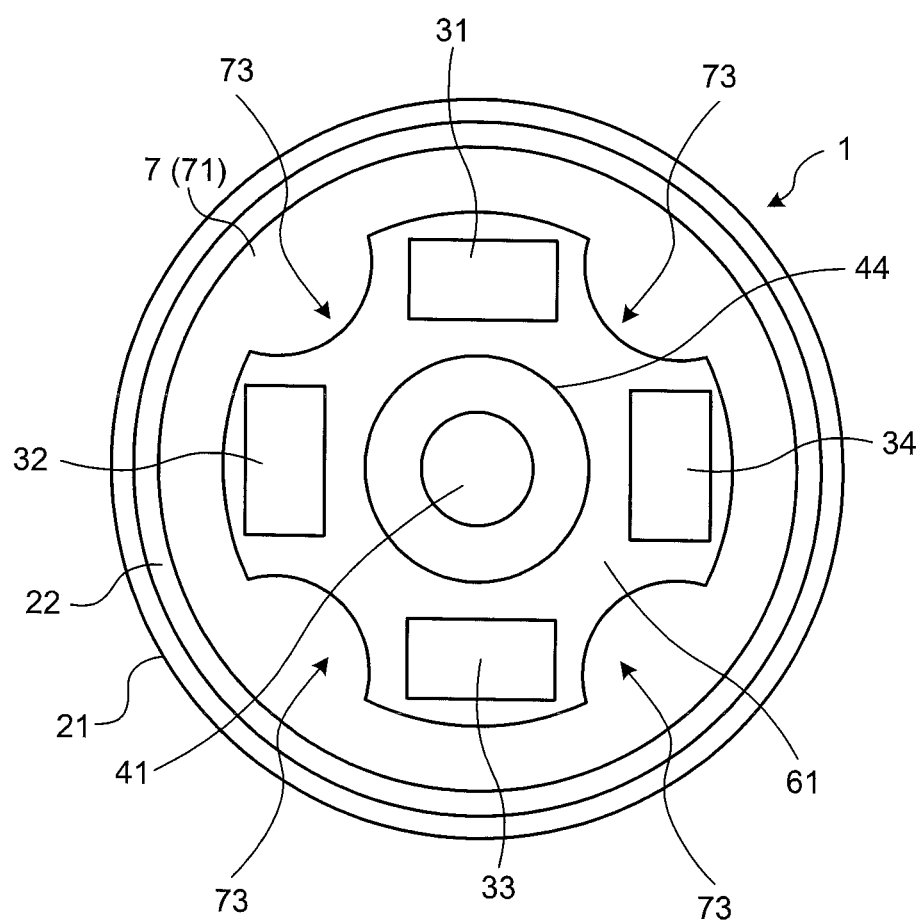
FIG. 2 is a schematic view of an exemplary internal structure of the capsule endoscope illustrated in FIG. 1, which is viewed from a front end side (left side) through an optical dome portion.
Figure 3:
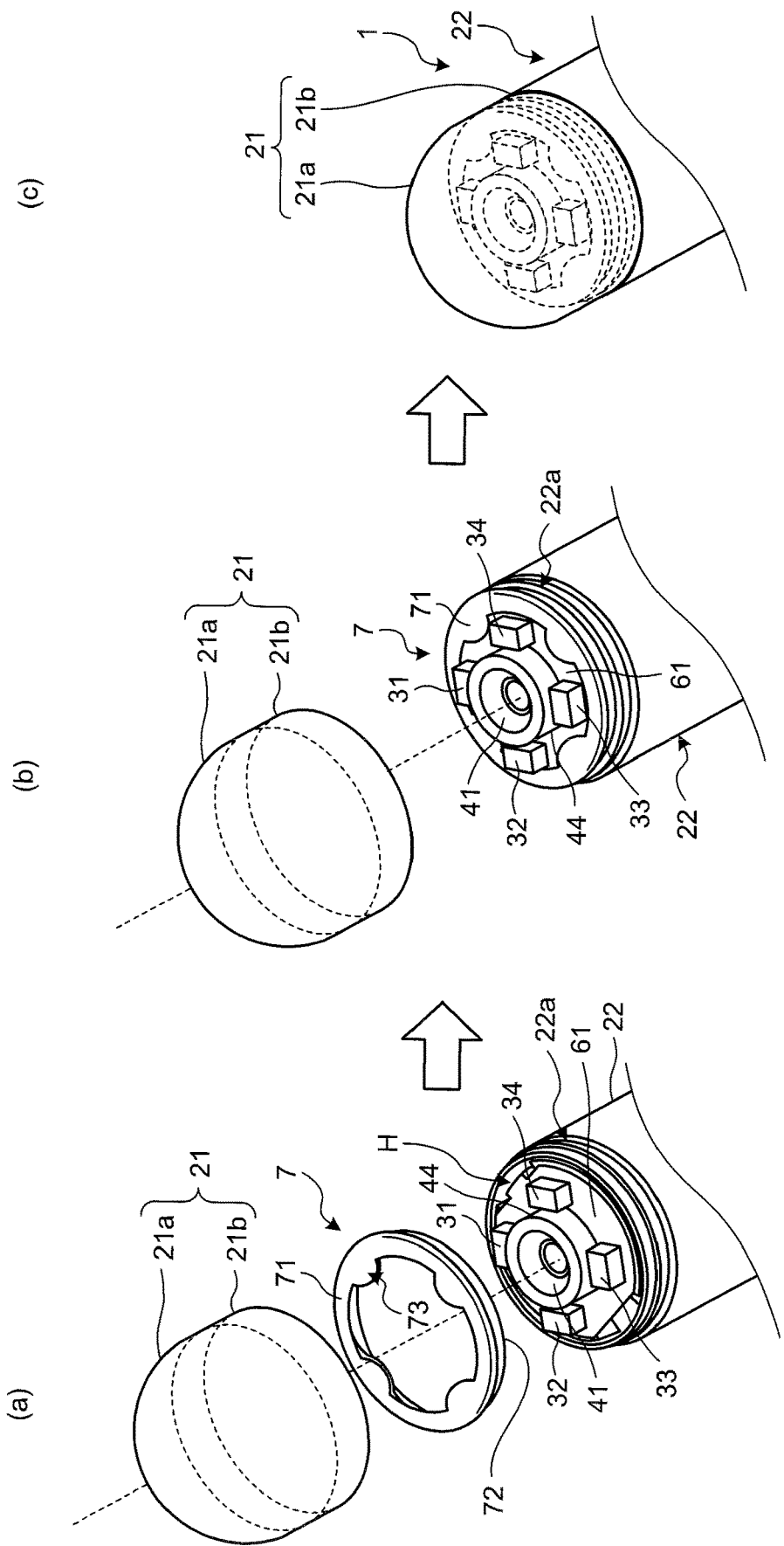
FIG. 3 is a perspective view illustrating main steps of a process of assembling the capsule endoscope illustrated in FIG. 1.

FIG. 1 is a vertical cross-sectional schematic view illustrating an exemplary configuration of the capsule endoscope according to the embodiment of the disclosure. FIG. 2 is a schematic view of an exemplary internal structure of the capsule endoscope illustrated in FIG. 1, which is viewed from a front end side (left side) through an optical dome portion. FIG. 3 is a perspective view illustrating main steps of a process of assembling the capsule endoscope illustrated in FIG. 1.

As illustrated in FIG. 1, a capsule endoscope 1 according to the embodiment of the disclosure is a monocular capsule endoscope, includes a capsule-shaped casing 2 formed in a sufficient size to be introduced into an organ of a subject, this casing 2 incorporates an information acquisition member for acquiring information about the subject, and the information acquisition member has the imaging function for capturing an in-vivo image, and the wireless communication function for wirelessly transmitting the captured in-vivo image to the outside. A broken line La represents a longitudinal central axis of the capsule endoscope 1, and a broken line Lb represents an axis extending in a transverse direction (radial direction) of the capsule endoscope 1, passing through a rear end of a hemispherical portion (dome hemispherical portion 21a) of an optical dome portion 21 described later. An imaging direction is oriented toward the left side (front end side) of FIG. 1. Furthermore, description will be made defining the right side of FIG. 1 as a rear end side.

As illustrated in FIGS. 1 to 3, the capsule endoscope 1 includes, as the information acquisition member, a plurality of light emitting elements 31 to 34 (light source), an optical unit 4 (optical system), an image sensor 5 (image sensor), a flexible circuit board 6, a control unit 8 (wireless communication member), a wireless communication unit 9 (wireless communication member), and a power supply unit 10, in the casing 2. Furthermore, the casing 2 incorporates a positioning member 7 defining positions of the light emitting elements 31 to 34, the optical unit 4, and the image sensor 5, relative to the optical dome portion 21 of the casing 2.

The casing 2 is a capsule-shaped casing having a sufficient size to be easily introduced into an organ of the subject, and includes the optical dome portion 21 (first casing) and a bottomed cylindrical case portion 22 (second casing). The optical dome portion 21 includes the hemispherical portion formed of a transparent member, and a cylindrical portion. The case portion 22 has an opening at one end.

The optical dome portion 21 includes the dome hemispherical portion 21a (hemispherical portion) having a hemispherical shape, and a dome cylindrical portion 21b (cylindrical portion) having a cylindrical shape. The dome cylindrical portion 21b includes an end portion connected to the dome hemispherical portion 21a on a plane passing through the center of the dome hemispherical portion 21a, and has a diameter the same as that of the dome hemispherical portion 21a. The optical dome portion 21 is transparent, and is formed of a biocompatible material (e.g., resin material such as polycarbonate, acrylic, cycloolefin polymer). The dome hemispherical portion 21a is a member positioned at one end of the capsule endoscope 1 in a longitudinal direction of the capsule endoscope 1. The dome hemispherical portion 21a has a specularly finished surface of an area included in a range of an optical system of the image sensor 5 in the optical dome portion 21.

In the case portion 22, a stepped structure 22a is formed around an outer peripheral surface of an end portion of the case portion 22 on a side of the opening, and the end portion of the dome cylindrical portion 21b is fitted to the outside of the stepped structure 22a. An outer diameter of a portion of the case portion 22 where the stepped structure 22a is positioned is substantially identical to an inner diameter of the dome cylindrical portion 21b of the optical dome portion 21, and a height of the stepped structure 22a in a direction of the axis Lb is substantially identical to a thickness of the end portion of the dome cylindrical portion 21b. Therefore, an outer diameter of the optical dome portion 21 is substantially identical to an outer diameter of a portion other than the stepped structure 22a of the case portion 22. Therefore, in the capsule endoscope 1, no stepped structure is formed on an outer surface of a joint between the optical dome portion 21 of the casing 2 and the case portion 22, and the capsule endoscope 1 can provide an outer surface having a smooth shape.

Specifically, an inner peripheral surface 21c of the end portion of the dome cylindrical portion 21b of the optical dome portion 21 abuts on an outer peripheral surface 22b of the case portion 22 on the side of the opening, and an end surface 21d of the end portion of the dome cylindrical portion 21b abuts on an end surface 22c of the stepped structure 22a of the case portion 22, and the end portion of the dome cylindrical portion 21b of the optical dome portion 21 is fitted to the stepped structure 22a of the case portion 22 on the side of the opening. This configuration defines a position of the optical dome portion 21 relative to the case portion 22, that is, a position of a spherical center of the optical dome portion 21 relative to the case portion 22. A UV adhesive is applied between the inner peripheral surface 21c of the dome cylindrical portion 21b of the optical dome portion 21, and the outer peripheral surface 22b of the case portion 22 on the side of the opening, the case portion 22 and the dome cylindrical portion 21b of the optical dome portion 21 are fitted to each other, and then, UV irradiation is performed through the optical dome portion 21 having transparency and positioned on the outside to make the casing 2 water-tight. Alternatively, laser irradiation is performed through the optical dome portion 21 having transparency and positioned on the outside to weld the inner peripheral surface 21c of the optical dome portion 21 and the outer peripheral surface 22b of the case portion 22 on the side of the opening, to each other, and the casing 2 is made water-tight. Note that, as described later, the optical dome portion 21 and the case portion 22 are fitted to each other, and the casing 2 is made water-tight, after the information acquisition member is incorporated into the case portion 22 while being positioned by the positioning member 7. The positioning member 7, which is described later, abuts on a part of an inner peripheral surface 22e of the case portion 22 on the side of the opening, and an end surface 22d of an opening portion of the case portion 22.

The light emitting elements 31 to 34 illuminate inside the subject near the front end. The light emitting elements 31 to 34 are for example light emitting elements such as an LED, and are mounted on an illumination circuit board 61. The illumination circuit board 61 is a substantially disk-shaped circuit board having an aperture, and is connected to the flexible circuit board 6. As illustrated in FIG. 2, the light emitting elements 31 to 34 are mounted on the illumination circuit board 61 to surround a lens frame 44 of the optical unit 4 inserted in the aperture of the illumination circuit board 61. The light emitting elements 31 to 34 emit for example white light, and illuminates inside the subject near the front end. Note that as long as illumination light having an amount sufficient to illuminate inside the subject near the front end is emitted, the number of light emitting elements is not limited to four.

The optical unit 4 focuses light reflected from inside the subject near the front end which is illuminated by the light emitting elements 31 to 34, and forms an image of the inside of the subject. The optical unit 4 includes, for example, lenses 41 and 42, a diaphragm portion 43 disposed between the lenses 41 and 42, and the lens frame 44 internally holding the lenses 41 and 42 and the diaphragm portion 43. The lenses 41 and 42 form an image of the inside of the subject near the front end on a light receiving surface 51 of the image sensor 5. The lens 42 has a leg portion, and the leg portion abuts on and is bonded to a peripheral edge portion of the light receiving surface 51 of the image sensor 5 to position the lenses 41 and 42 and the image sensor 5. The diaphragm portion 43 adjusts the brightness of the reflected light focused by the lens 41 and the lens 42. The lens frame 44 has a shape in which two cylinders having different diameters are connected by a disk. A cylindrical portion 44a having a small diameter and positioned on the front end side internally holds the lenses 41 and 42 and the diaphragm portion 43, inserted into the aperture of the illumination circuit board 61, and partially projects toward the front end side. A disk portion 44b is disposed so that a surface of the disk portion 44b on the front end side abuts on a back surface of the illumination circuit board 61. A cylindrical portion 44c having a large diameter and positioned on the rear end side is disposed so that an outer peripheral surface 44d of the cylindrical portion 44c (outside surface of the information acquisition member) abuts on an inner peripheral surface 72b of a projecting portion 72 of the positioning member 7. Incidentally, for example, the disk portion 44b and the cylindrical portion 44c are formed so that the disk portion 44b and a side wall of the cylindrical portion 44c of the lens frame 44 are partially cut out, and thereby an opening portion H (gap) is formed partially between the inner peripheral surface 22e of the case portion 22 on the side of the opening (inside surface of the second casing on the side of the opening), and the disk portion 44b of the lens frame 44. An extending portion 63 extending from the illumination circuit board 61 is bent toward the rear end side to be inserted into the opening portion H, and is connected to an imaging circuit board 62 described later. The illumination circuit board 61 has a surface which is arranged to abut on a surface 71b on the rear end side of an annular portion 71 of the positioning member 7.

The image sensor 5 is an image sensor such as a CCD or CMOS having the light receiving surface 51 on which photoelectric conversion elements are arranged in a matrix, and captures an image of the inside of the subject formed by the optical unit 4. The image sensor 5 is mounted to the imaging circuit board 62. The imaging circuit board 62 is a substantially disk-shaped circuit board having an aperture, and connected to the flexible circuit board 6. The lens 42 and the light receiving surface 51 of the image sensor 5 are opposed to each other, through the aperture of the imaging circuit board 62.

The flexible circuit board 6 is connected to the illumination circuit board 61 and the imaging circuit board 62 described above, and is connected to a control circuit board 82 and a wireless communication circuit board 91 described later. The illumination circuit board 61 is a substantially disk-shaped flexible circuit board on which a circuit for achieving the illumination function for an object near the front end of the capsule endoscope 1 is formed. As described above, on the surface of the illumination circuit board 61, the light emitting elements 31 to 34 are mounted, and at the center of the surface of the illumination circuit board 61 surrounded by the light emitting elements 31 to 34, an aperture portion is formed to insert the cylindrical portion 44a of the lens frame 44. Note that, the cylindrical portion 44a of the lens frame 44 holds the lens 42 having the leg portion abutting on the image sensor 5. The illumination circuit board 61 is electrically connected to the imaging circuit board 62 through the extending portion 63 extending from an outer edge portion of the illumination circuit board 61.

The imaging circuit board 62 is a substantially disk-shaped flexible circuit board on which a circuit for achieving an imaging function for the in-vivo image on the front end side is formed. On a surface of the imaging circuit board 62, the image sensor 5 is flip-chip mounted, and a circuit component such as a capacitor is further mounted. Furthermore, an aperture portion for leading incident light reflected from the inside of the subject near the front end, to the light receiving surface 51 of the image sensor 5 is formed in the imaging circuit board 62. The imaging circuit board 62 has an outer edge portion partially extending as an extending portion 64, and bent to the rear end side to be connected to the flexible circuit board 6.

The positioning member 7 fixes a positional relationship of the optical dome portion 21, the light emitting elements 31 to 34, and the optical unit 4 to determine suitable positions of the light emitting elements 31 to 34, the optical unit 4, and the image sensor 5 relative to the optical dome portion 21. The annular portion 71 positions the light emitting elements 31 to 34 and the optical unit 4 relative to the optical dome portion 21, in a longitudinal direction indicated by the central axis La, and the projecting portion 72 positions the light emitting elements 31 to 34 and the optical unit 4 relative to the optical dome portion 21, in the transverse direction indicated by the axis Lb, and the annular portion 71 and the projecting portion 72 are configured to be integrated with each other.

The annular portion 71 has substantially a disk shape having an aperture. The annular portion 71 has an outer diameter smaller than an inner diameter of the end portion of the dome cylindrical portion 21b of the optical dome portion 21, and larger than an inner diameter of the end portion of the case portion 22 on the side of the opening. The aperture of the annular portion 71 has a shape set so that the lens frame 44 and the light emitting elements 31 to 34 can project from the aperture.

The annular portion 71 has a surface 71a (first abutment surface) on the outer peripheral side of a rear end side surface (back surface), and the end surface 22d of the opening portion of the case portion 22 abuts on the surface 71a. Since the inner peripheral surface 21c of the dome cylindrical portion 21b of the optical dome portion 21 is fitted on the outer peripheral surface 22b of the case portion 22 on the side of the opening, the surface 71a of the annular portion 71 abuts on the end surface 22d of the case portion 22, and a position of the annular portion 71 relative to the optical dome portion 21 in a direction of the central axis La is defined through the case portion 22.

A peripheral edge portion of the surface of the illumination circuit board 61 constituting the information acquisition member abuts on the surface 71b (second abutment surface) on the inner peripheral side of the back surface of the annular portion 71. The surfaces 71a and 71b are positioned on the same surface of the annular portion 71. Accordingly, through the positioning member 7, the positions of the illumination circuit board 61, the light emitting elements 31 to 34, the lens frame 44, the lenses 41 and 42, and the image sensor 5 are defined relative to the optical dome portion 21, in the direction of the central axis La. In this configuration, the light emitting elements 31 to 34 are mounted on the surface of the illumination circuit board 61, the disk portion 44b of the lens frame 44 abuts on the back surface of the illumination circuit board 61, the lenses 41 and 42 are held by the lens frame 44, and the leg portion of the lens 42 abuts on the image sensor 5. Note that the annular portion 71 is set to have a width sufficient to cover at least the opening portion H between the inner peripheral surface 22e of the case portion 22, and the disk portion 44b of the lens frame 44. The annular portion 71 is assembled to the casing 2 to close the opening portion H, and an inner space of the optical dome portion 21 is isolated from an inner space of the case portion 22 in which the information acquisition member is incorporated. Additionally, the annular portion 71 is provided with protruding surfaces 73 (see FIG. 2) positioned between the light emitting elements 31 to 34 and protruding toward the aperture, and an area of the annular portion 71 abutting on the surface of the illumination circuit board 61 is increased to stabilize a position of the illumination circuit board 61 in the direction of the central axis La.

The projecting portion 72 has a cylindrical shape, and has an outer diameter substantially the same as an inner diameter of the inner peripheral surface 22e of the case portion 22 on the side of the opening. Therefore, the outer diameter of the projecting portion 72 is smaller than the outer diameter of the annular portion 71. The projecting portion 72 has an inner diameter substantially the same as an outer diameter of the cylindrical portion 44c of the lens frame 44. The projecting portion 72 (third abutment surface) has an outer peripheral surface 72a on which the inner peripheral surface 22e of the case portion 22 on the side of the opening (inside surface of the second casing on the side of the opening) abuts. The outer peripheral surface 44d of the cylindrical portion 44c of the lens frame 44 (outside surface of the information acquisition member) abuts on the inner peripheral surface 72b of the projecting portion 72 (fourth abutment surface). In other words, a front end of the projecting portion 72 fills a gap between the cylindrical portion 44c of the lens frame 44 and the case portion 22, and defines the position of the lens frame 44 relative to the optical dome portion 21 in the direction of the axis Lb (radial direction), through the case portion 22. That is, the projecting portion 72 defines the positions of the optical unit 4 and the image sensor 5 relative to the optical dome portion 21, in the direction of the axis Lb through the case portion 22 so that the pupil center of the optical unit 4, and the spherical center of the optical dome portion 21 are coincident with the central axis La.

The control unit 8 includes an electronic component group 81 for controlling the imaging function and the wireless communication function, and the control circuit board 82 of a substantially disk shape to mount the electronic component group 81 on the surface thereof. Circuit components of various power supply systems such as a magnetic switch, which are described later, are illustrated on a back surface of the control circuit board 82. The Control unit 8 is electrically connected to the illumination circuit board 61, the imaging circuit board 62, and the wireless communication circuit board 91 which is described later, through the flexible circuit board 6 connected to the control circuit board 82 and the wireless communication circuit board 91, and controls the light emitting elements 31 to 34 mounted on the illumination circuit board 61, the image sensor 5 mounted on the imaging circuit board 62, and the wireless communication unit 9 mounted on the wireless communication circuit board 91. The Control unit 8 has various parameters about image processing, and an image processing function for sequentially processing the image signal including the in-vivo image near the front end captured by the image sensor 5.

The wireless communication unit 9 performs modulation or the like on the image signal including the in-vivo image captured by the image sensor 5 to generate a wireless signal, and transmits the generated wireless signal outside. The wireless communication unit 9 includes the wireless communication circuit board 91, an electronic component 92 mounted on the wireless communication circuit board 91 and processing each of the in-vivo images captured by the image sensor 5, and an antenna 93 for wirelessly transmitting the signal processed by the electronic component 92, to the outside.

The power supply unit 10 supplies operation power to the light emitting elements 31 to 34, the image sensor 5, the control unit 8, and the wireless communication unit 9. The power supply unit 10 incorporates a contact spring 10c, and a battery 10a is electrically connected to the circuit components of the power supply system on the control circuit board 82, through the contact spring 10c and the flexible circuit board 6.

In the capsule endoscope 1, the wireless communication unit 9, the power supply unit 10, the control unit 8, the image sensor 5 to which the optical unit 4 is mounted, and light emitting elements 31 to 34, which are connected to the flexible circuit board 6, the imaging circuit board 62, and the illumination circuit board 61, are inserted into the case portion 22 from the opening of the case portion 22, and then the positioning member 7 is fitted into the case portion 22 to cover the illumination circuit board 61, as illustrated in (a) of FIG. 3 and (b) of FIG. 3. Thus, the opening portion H is closed by the annular portion 71 of the positioning member 7. Next, the dome cylindrical portion 21b of the optical dome portion 21 is fitted on the outside of the stepped structure 22a of the case portion 22, the UV bonding or laser welding is performed through the optical dome portion 21, then, as illustrated in (c) of FIG. 3, the dome cylindrical portion 21b of the optical dome portion 21 is fixed on the outside of the case portion 22, and the capsule endoscope 1 is assembled.

In the capsule endoscope 1 according to this embodiment, the surface of the illumination circuit board 61 abuts on the surface 71b on the rear end side of the annular portion 71 of the positioning member 7. The dome cylindrical portion 21b of the optical dome portion 21 is fitted on the outside of the case portion 22, and the end surface 22d of the case portion 22 abuts on the surface 71a on the rear end side of the annular portion 71 of the positioning member 7. Therefore, in the capsule endoscope 1, the lenses 41 and 42 and the light receiving surface 51 of the image sensor 5 are defined to be disposed at preferable positions relative to the optical dome portion 21, in the direction of the central axis La, through the positioning member 7 and the case portion 22.

Furthermore, in the capsule endoscope 1 according to the embodiment, the outer peripheral surface 44d of the cylindrical portion 44c of the lens frame 44 abuts on the inner peripheral surface 72b of the projecting portion 72, and the inner peripheral surface 22e of the opening of the case portion 22 abuts on the outer peripheral surface 72a of the projecting portion 72. Owing to this configuration, in the capsule endoscope 1, the lenses 41 and 42 and the light receiving surface 51 of the image sensor 5 are defined to be disposed at preferable positions relative to the optical dome portion 21, in the direction of the axis Lb (radial direction), through the case portion 22. As a result, in the capsule endoscope 1, the pupil center (optical axis) of the lenses 41 and 42 and the image sensor 5 and the spherical center of the dome hemispherical portion 21a of the optical dome portion 21 can accurately coincide with the longitudinal central axis La, and flare can be suppressed.

Furthermore, the capsule endoscope 1 defines a relative position between the casing 2 and the information acquisition member in the casing 2 by using the positioning member 7 being separated. Therefore, according to the capsule endoscope 1, an abutment surface for positioning the information acquisition member does not need to be provided at end portions of the optical dome portion 21 and the case portion 22, and thus the wall thickness of the optical dome portion 21 and the wall thickness of the case portion 22 can be reduced. Thus, according to the capsule endoscope 1, the wall thicknesses of the optical dome portion 21 and the case portion 22 can be reduced to reduce the weight thereof, and a sufficient inner space can be ensured. Therefore, according to the capsule endoscope 1, a sufficient space can be ensured for the information acquisition member, gives a wide choice of components for the information acquisition member, and allows high performance of the capsule endoscope 1. Furthermore, the capsule endoscope 1 can be designed so that the outer diameter of the optical dome portion 21 is substantially the same as the outer diameter of a portion other than the outer peripheral surface 22b of the opening of the case portion 22. Thus, no stepped structure is formed on the outer surface of the joint between the optical dome portion 21 of the casing 2 and the case portion 22, and the capsule endoscope 1 can provide the outer surface of a smooth shape. The smooth shape of the outer surface of the capsule endoscope 1 has the effect of preventing the capsule endoscope 1 from being caught in the mucosa, and preventing residue or the like in the body cavity from adhering to the capsule endoscope 1, in addition to ease of swallowing by the subject.

Furthermore, in the capsule endoscope 1, since the dome cylindrical portion 21b of the optical dome portion 21 is fitted on the outside of the case portion 22, the UV bonding or laser welding can be performed through the optical dome cylindrical portion 21b having transparency and positioned on the outside, and a bonding method by which watertightness is ensured in a short time can be adopted. The method can be performed in a short time, in comparison with fixing the case portion and the dome portion to each other by thermal bonding using a thermosetting adhesive.

Furthermore, in the capsule endoscope 1, the annular portion 71 of the positioning member 7 closes the opening portion H to isolate the inner space of the optical dome portion 21 from the inner space of the case portion 22 in which the information acquisition member is incorporated. Therefore, after a main body of the capsule endoscope 1 is made water-tight, no dust generated from the information acquisition member enters the inner space of the optical dome portion 21. When the dust adheres to the optical dome portion 21, the dust appears in an image unexpectedly, and the image is damaged, but, according to the capsule endoscope 1, it is possible to eliminate the damage.

First Modification of Embodiment

Figure 4:
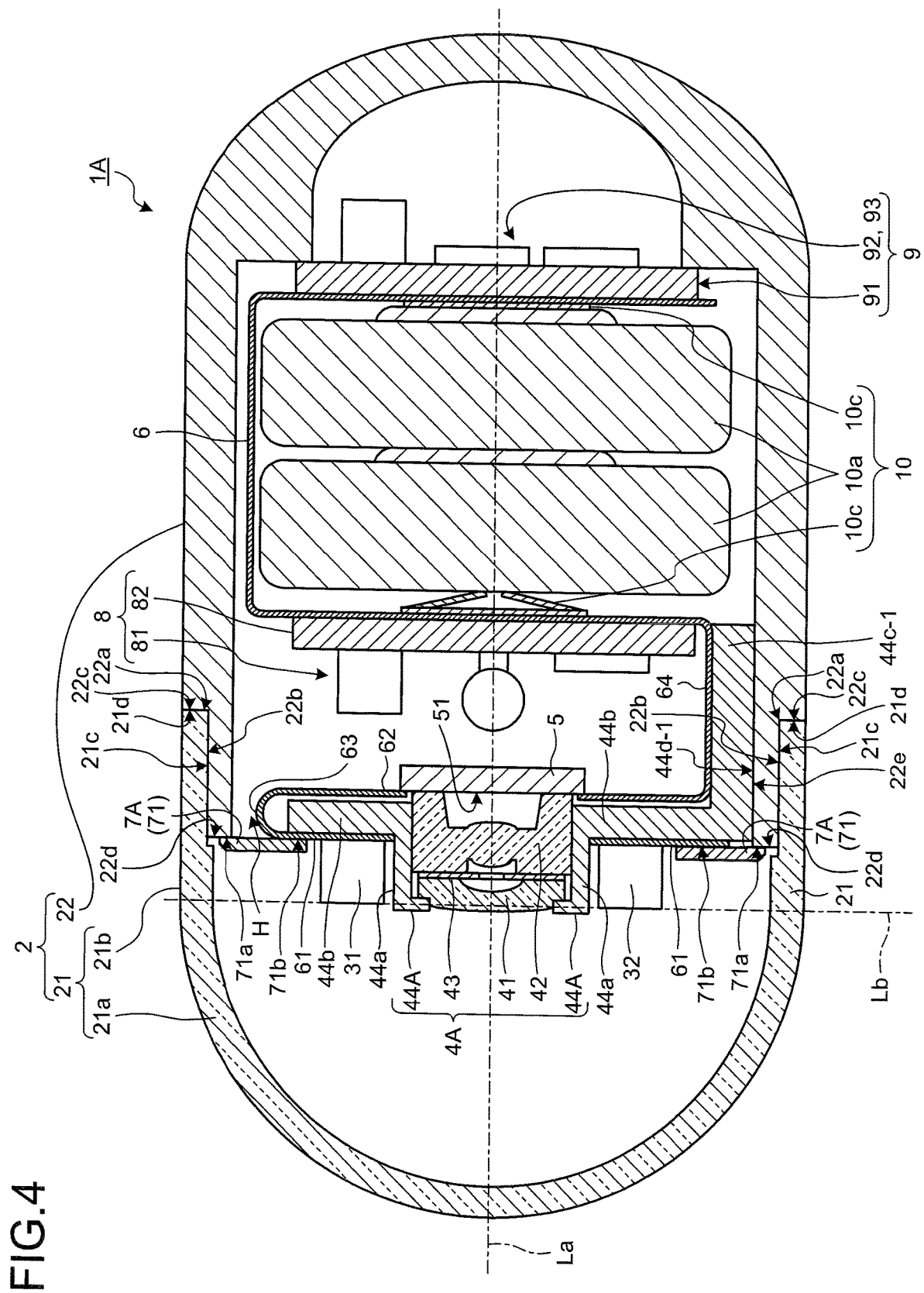
FIG. 4 is a vertical cross-sectional schematic view illustrating an exemplary configuration of a capsule endoscope according to a first modification of the embodiment.

FIG. 4 is a vertical cross-sectional schematic view illustrating an exemplary configuration of a capsule endoscope according to a first modification of the embodiment of the disclosure.

As in a capsule endoscope 1A according to the first modification of the embodiment illustrated in FIG. 4, when a cylindrical portion 44c-1 has a thickness set so that an outer peripheral surface 44d-1 of the cylindrical portion 44c-1 of a lens frame 44A constituting an optical unit 4A abuts on the inner peripheral surface 22e of the case portion 22, the positions of the lenses 41 and 42 and the light receiving surface 51 of the image sensor 5 can be determined relative to the optical dome portion 21, in the direction of the axis Lb, through the case portion 22 and the lens frame 44A abutting on the case portion 22, and a positioning member 7A from which the projecting portion 72 is removed can be adopted.

Second Modification of Embodiment

Figure 5:
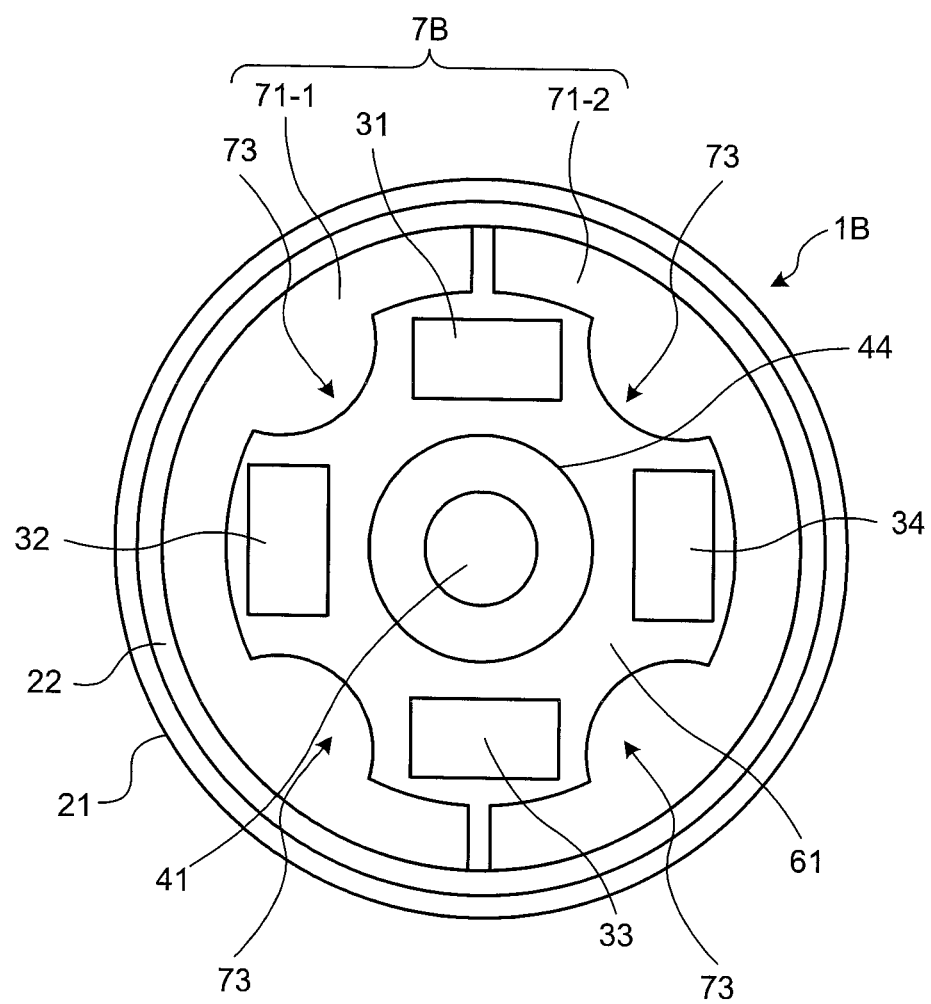
FIG. 5 is a schematic view of an exemplary internal structure of a capsule endoscope according to a second modification of the embodiment, which is viewed from the front end side through the optical dome portion.
Figure 6:
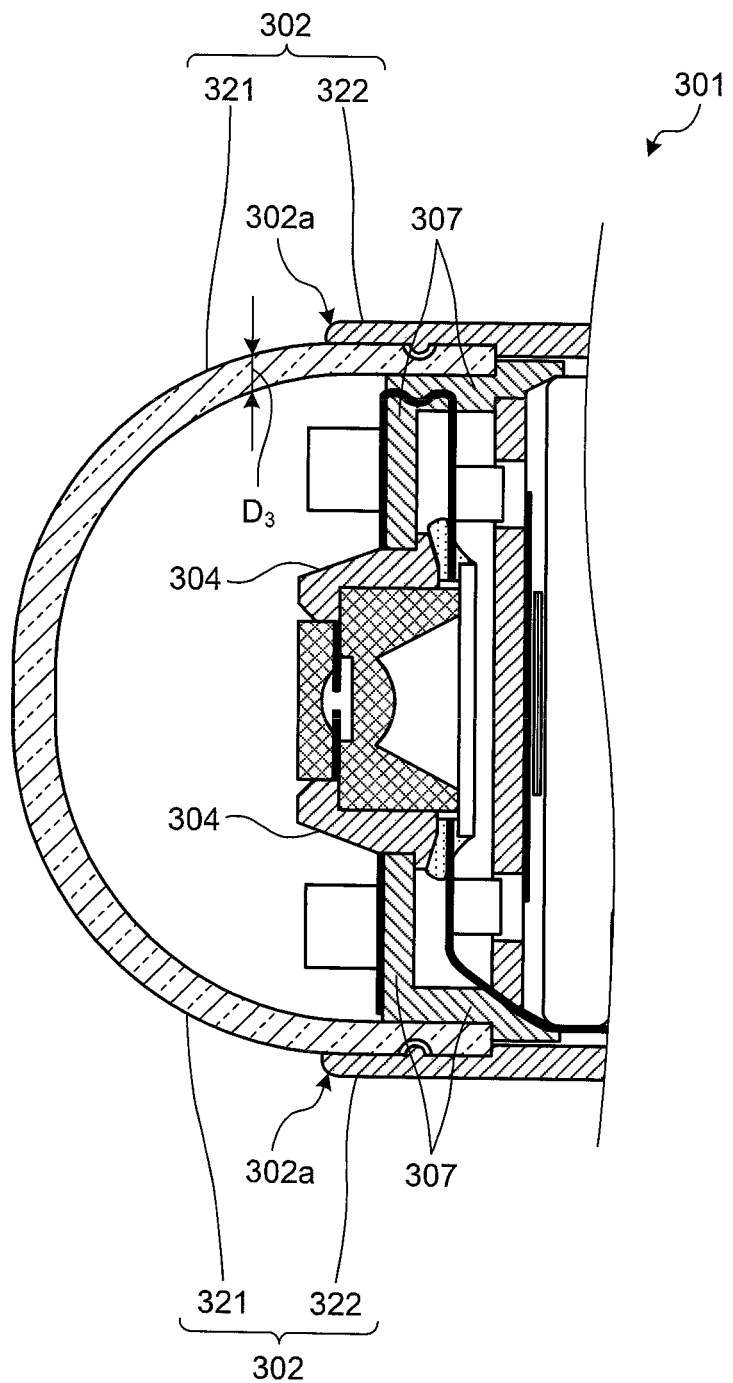
FIG. 6 is a cross-sectional view illustrating a configuration of a main portion of a conventional capsule endoscope.
Figure 7:
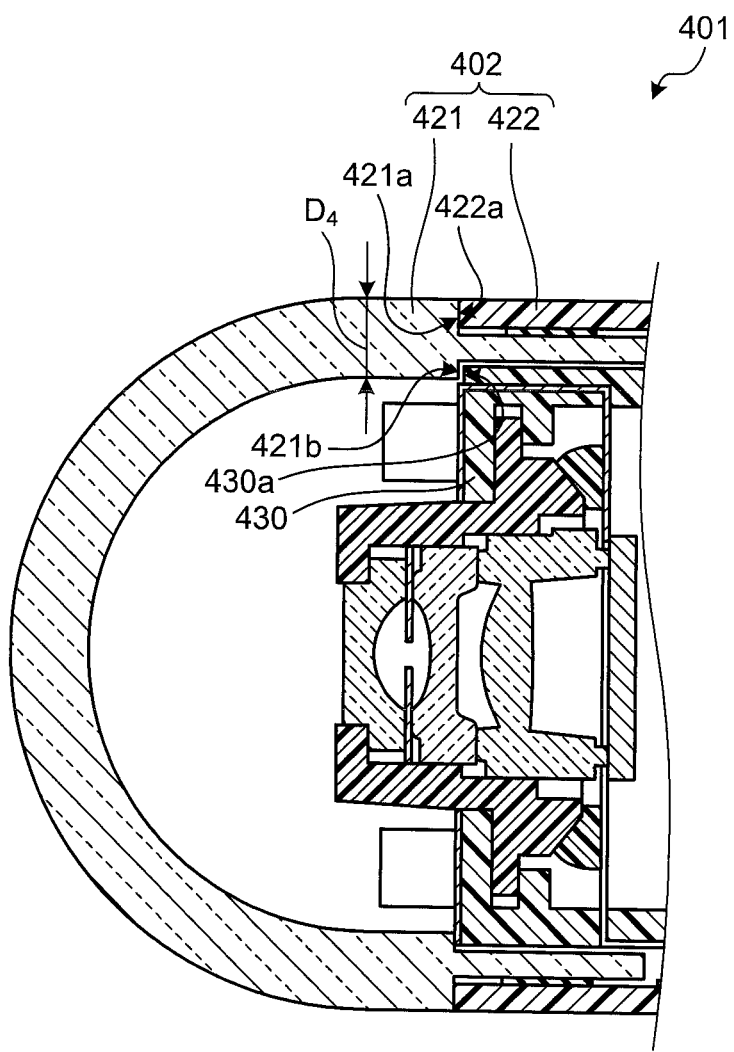
FIG. 7 is a cross-sectional view illustrating a configuration of a main portion of a conventional capsule endoscope.
Figure 8:
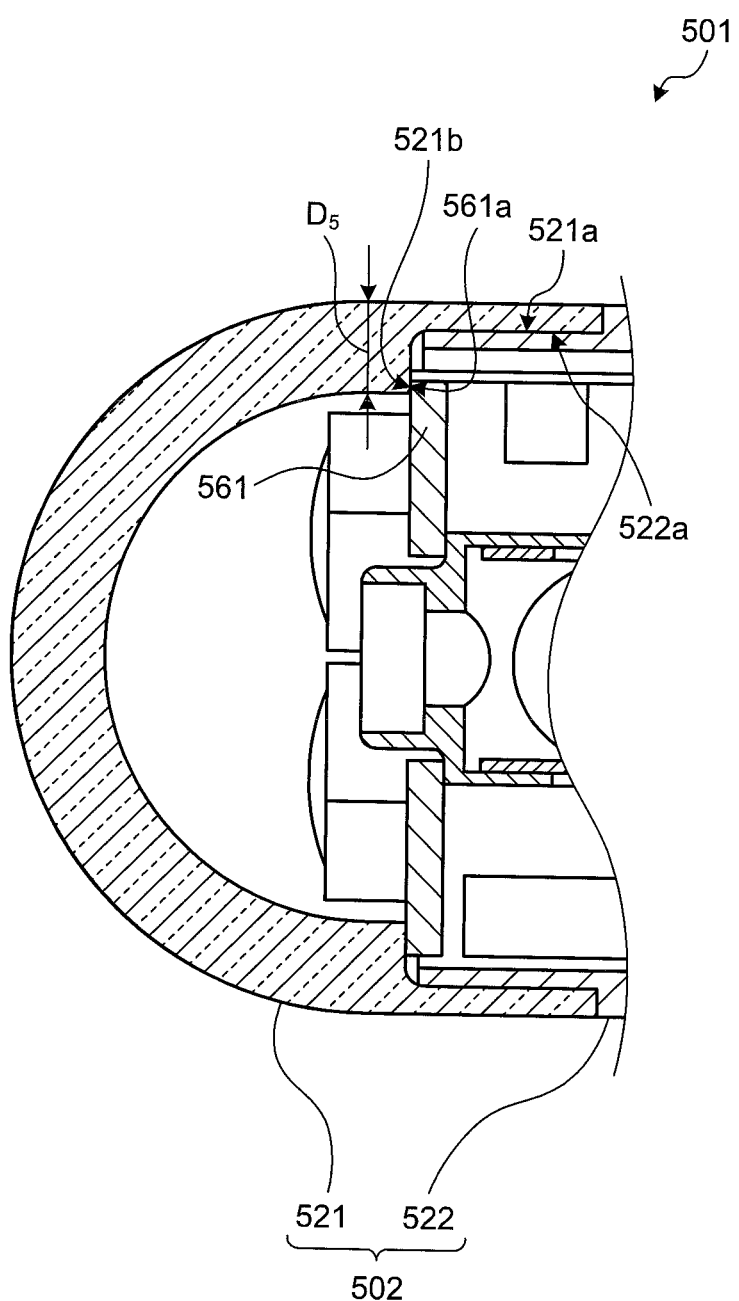
FIG. 8 is a cross-sectional view illustrating a configuration of a main portion of a conventional capsule endoscope.

FIG. 5 is a schematic view of an exemplary internal structure of a capsule endoscope according to a second modification of the embodiment, which is viewed from the front end side through the optical dome portion. As in a capsule endoscope 1B according to a second modification of the embodiment of FIG. 5, the positioning member is not necessarily integrally formed, and can be constituted by a plurality of members, such as a positioning member 7B including a first positioning member 71-1 and a second positioning member 71-2.

As the embodiment of the disclosure described above, the capsule endoscopes 1, 1A, and 1B being a monocular capsule endoscope have been described, but, as a matter of course, the present embodiment can also be applied to a pantoscopic capsule endoscope. In the pantoscopic capsule endoscope, a cylindrical case portion has openings at both ends, and the optical units 4 and the image sensors 5 may be assembled to the front end side and the rear end side, respectively, while being positioned by the positioning member 7 so that the optical dome portions are externally fitted to both ends of the case portion.

Furthermore, in the embodiment of the disclosure described above, the capsule endoscopes 1, 1A, and 1B acquiring the in-vivo image as an example of the in-vivo information have been described, but, as a matter of course, the disclosure is not limited to the capsule endoscopes 1, 1A, and 1B, and may employ a pH measurement capsule for measuring pH information in a living body as the in-vivo information. Furthermore, a capsule-shaped temperature measurement device may be employed which measures temperature information of a living body, as the in-vivo information. Furthermore, a capsule-shaped drug administration device may be employed which has a function of scattering or injecting a medicine into a living body. Furthermore, a capsule-shaped biopsy device may be employed which collects a material in a living body (body tissue or the like) as the in-vivo information.

As described above, the capsule medical device according to the disclosure positions the optical pupil center of the optical unit constituting the information acquisition member for acquiring subject information, and the spherical center of the hemispherical portion of the transparent casing, reducing the wall thickness of the casing having transparency and the wall thickness of the cylindrical casing to reduce the weight, can adopt the bonding method by which water-tightness is ensured in a short time, and has the outer surface of a smooth shape. Thus, the capsule medical device is useful to achieve a capsule medical device having an outer surface of a smooth shape.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical device comprising:
 a capsule-shaped casing including:
  a first casing including:
   a hemispherical portion formed of a transparent member; and
   a cylindrical portion including an end portion connected to the hemispherical portion and having a diameter the same as that of the hemispherical portion; and
  a second casing that is a cylindrical casing having an on one side, the cylindrical portion having an outer surface, and an inner surface having a constant diameter, the inner surface terminating in an edge, the edge being offset from the inner surface, an information acquisition member being disposed in the opening, wherein the information acquisition member comprising at least an image sensor; and
 a positioning member including:
  a first abutment surface configured to abut on the edge; and
  a second abutment surface configured to abut on a first surface of the information acquisition member, the first surface intersecting with a longitudinal axis of the second casing.

2. The capsule medical device according to claim 1, wherein the second casing has a stepped structure at the outer surface proximate to the opening, the stepped structure having a height the same as a thickness of the end portion of the cylindrical portion.

3. The capsule medical device according to claim 1, wherein the positioning member further includes a third abutment surface configured to abut on the interior surface, and a fourth abutment surface configured to abut on an outside surface of the information acquisition member.

4. The capsule medical device according to claim 3, wherein
 the positioning member includes a projecting portion, and
 the third abutment surface and the fourth abutment surface are provided at the projecting portion.

5. The capsule medical device according to claim 1, wherein
 the positioning member includes an annular portion, and
 the first abutment surface and the second abutment surface are provided at the annular portion.

6. The capsule medical device according to claim 5, wherein the first abutment surface and the second abutment surface are positioned on a same surface of the annular portion.

7. The capsule medical device according to claim 5, wherein
 a gap is formed partially between the interior surface and the information acquisition member, and
 the positioning member has a width so that the annular portion fills at least the gap.

* * * * *